(12) United States Patent
Gadzey

(10) Patent No.: US 10,737,055 B1
(45) Date of Patent: Aug. 11, 2020

(54) METHOD OF TREATING A STRESS-RELATED OR SLEEP-RELATED CONDITION

(71) Applicant: Anthony Gadzey, Auburn, AL (US)

(72) Inventor: Anthony Gadzey, Auburn, AL (US)

(*) Notice: Subject to any disclaimer, the term of this patent is extended or adjusted under 35 U.S.C. 154(b) by 0 days.

(21) Appl. No.: 16/424,091

(22) Filed: May 28, 2019

(51) Int. Cl.
*A61M 21/02* (2006.01)
*A61M 16/00* (2006.01)
*A61F 5/56* (2006.01)
*A61M 16/06* (2006.01)
*A61B 5/00* (2006.01)
*A61M 21/00* (2006.01)

(52) U.S. Cl.
CPC .............. *A61M 21/02* (2013.01); *A61F 5/56* (2013.01); *A61M 16/0003* (2014.02); *A61B 5/4806* (2013.01); *A61M 16/0683* (2013.01); *A61M 2021/0066* (2013.01); *A61M 2230/50* (2013.01)

(58) Field of Classification Search
CPC .............. A61F 2007/0007; A61F 7/02; A61F 2007/0054; A61F 2007/0002; A61F 2007/0295; A61F 7/007; A61F 7/0085; A61M 2021/0066; A61M 21/02; A61M 2021/0083; A61M 2210/06; A61M 2210/0693; A61M 2205/3368; A61M 2210/0687
See application file for complete search history.

(56) References Cited

U.S. PATENT DOCUMENTS

| | | | |
|---|---|---|---|
| 1,554,681 | A | 9/1925 | Merke |
| 2,017,027 | A | 8/1931 | Forrest |
| 3,362,180 | A | 1/1968 | Eiseman, Jr. |
| 3,695,066 | A | 10/1972 | Doyel |
| 4,883,942 | A | 11/1989 | Robak, Sr. et al. |
| 5,168,576 | A | 12/1992 | Krent et al. |
| 5,423,087 | A | 6/1995 | Krent et al. |
| 5,636,377 | A | 6/1997 | Wiener |
| 5,689,836 | A | 11/1997 | Fee et al. |
| 6,195,809 | B1 | 3/2001 | Garcia |
| 6,629,964 | B1 | 10/2003 | Ono et al. |
| 7,181,918 | B2 | 2/2007 | Reinders |
| 8,291,612 | B2 | 10/2012 | Ferguson |
| 8,409,199 | B2 | 4/2013 | Herzon |
| 8,932,198 | B1 * | 1/2015 | You ..................... A61B 17/545 600/27 |
| 2004/0055072 | A1 * | 3/2004 | Lee .................... A41D 13/0053 2/171 |
| 2009/0287280 | A1 | 11/2009 | Wong et al. |

FOREIGN PATENT DOCUMENTS

WO     2008036283     3/2008

* cited by examiner

*Primary Examiner* — Christine H Matthews
(74) *Attorney, Agent, or Firm* — Nicholas J. Landau; Bradley Arant Boult Cummings LLP

(57) ABSTRACT

Devices and methods for the prevention and treatment of disorders related to stress and poor sleep are provided. A headgear device is provided that delivers heated water vapor to the crown of the wearer's head, which has been observed to facilitate sleep and reduce the symptoms of stress. Methods of facilitating sleep and reducing stress are provided that involve exposing the crown to heated water vapor. Further embodiments of the device and methods for use thereof provide relief to other parts of the body, such as joints and back muscles.

16 Claims, 3 Drawing Sheets

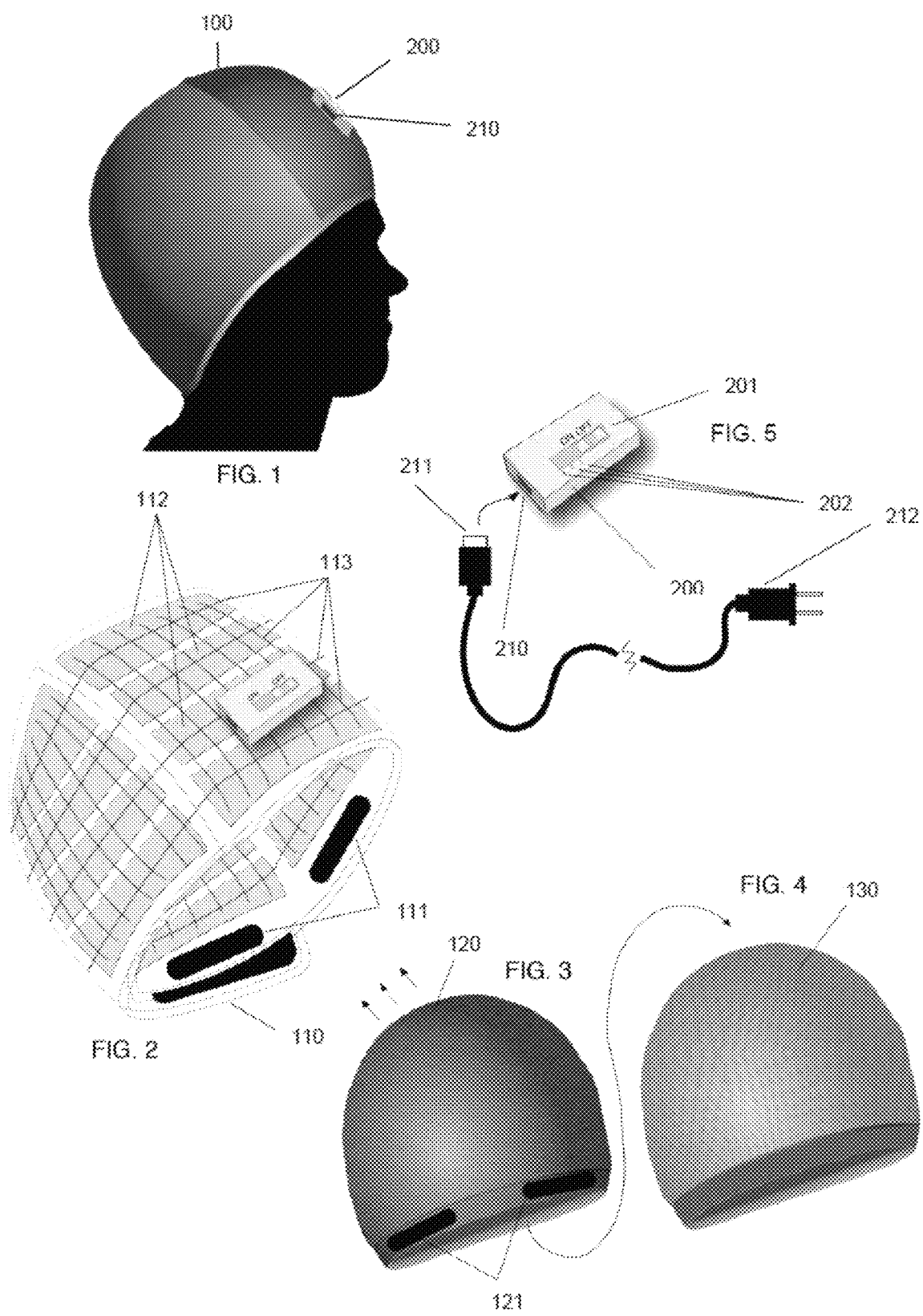

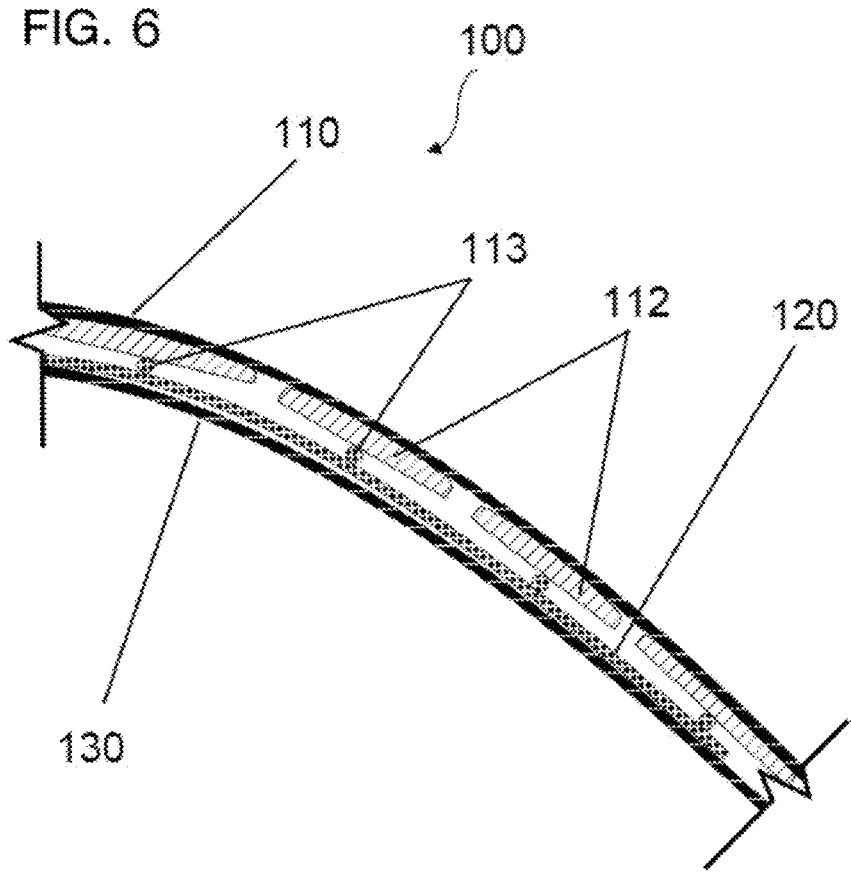

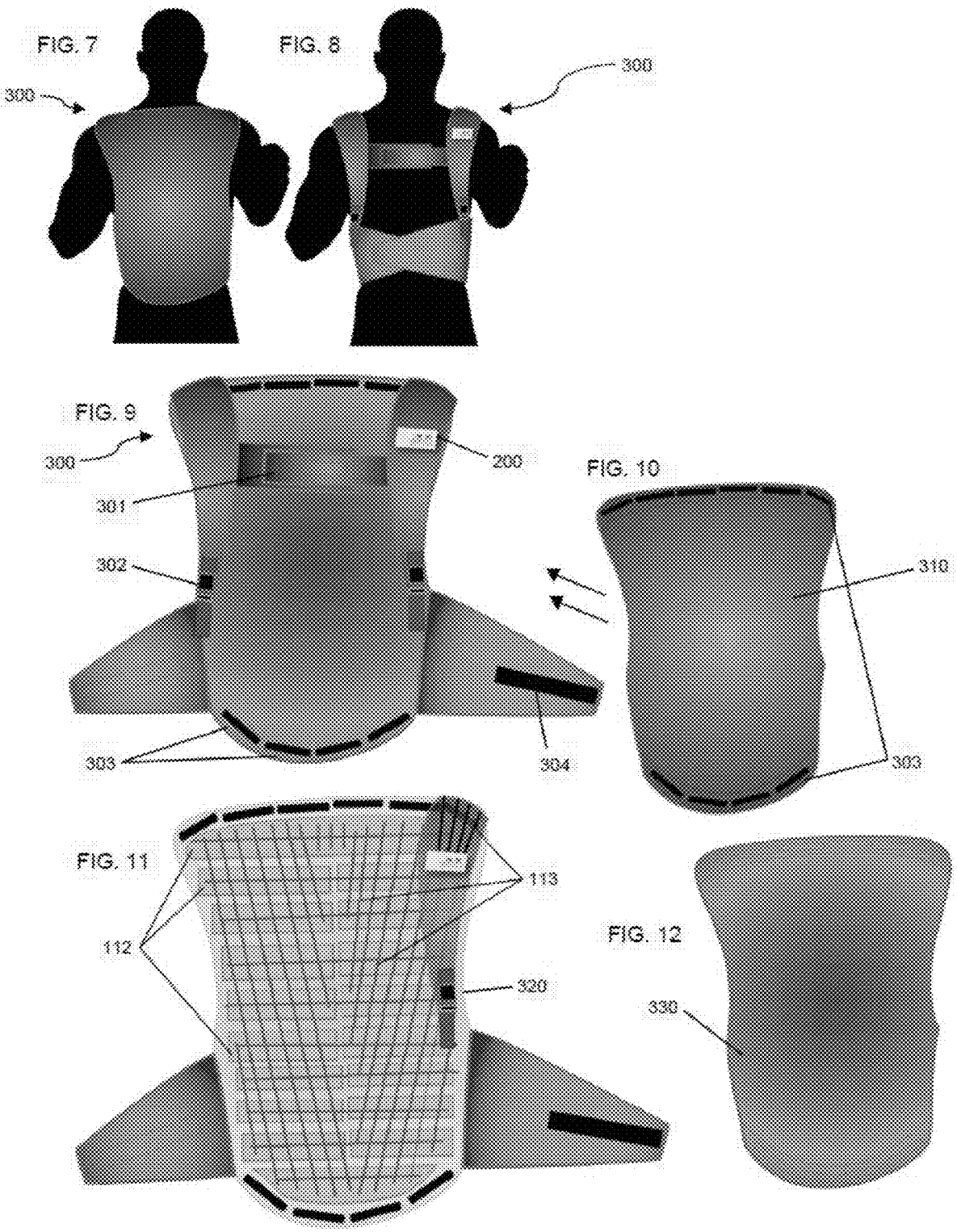

METHOD OF TREATING A STRESS-RELATED OR SLEEP-RELATED CONDITION

FIELD

The present disclosure relates generally to medical devices and sleep aids, and specifically headgear devices of this type.

BACKGROUND

Sleep and mental wellbeing are closely intertwined. Many illnesses and disorders (both psychological and physical) cause sleep disruption. Insufficient sleep in turn causes numerous psychological and physical symptoms of varying severity, generally depending on the severity of the sleep deprivation. Such symptoms include trouble focusing the attention, lack of attention to sensory input, increased human error resulting in accidents, longer reaction times, excessive yawning, moodiness, fatigue, irritability, depression, learning difficulties, forgetfulness, anxiety, lack of motivation, clumsiness, increased appetite, reduced libido, weakened immune system, increased insulin release, increased risk of cardiovascular disease, increased risk of hypertension, increased stroke risk, and increased risk for diabetes. Severe sleep deprivation can result in psychosis and hallucination.

Stress-related conditions have numerous causes, including sleep deprivation. Lack of sleep can leave a person vulnerable to stress, and stress can cause insomnia. Numerous stress-related disorders are recognized, including post-traumatic stress disorder (PTSD), acute stress disorder (ASD), depression, anxiety, obsessive-compulsive disorder (OCD), and eating disorders. Stress also causes several recognized physical symptoms, many of which overlap with the symptoms of sleep deprivation. These include lack of energy, headache, upset stomach, diarrhea, constipation, nausea, muscle aches (such as back pain and joint pain), chest pain, tachycardia, insomnia, vulnerability to infection, reduced libido, sexual dysfunction, tinnitus, excessive perspiration (such as on the hands and feet), xerostomia, dysphagia, and bruxism.

Although sleep disorders and stress are widespread in the United States and many other countries, effective treatments are limited. Sleep-inducing drugs generally provide low-quality sleep or have serious side effects such as sleep walking. Drugs for the treatment of stress and anxiety have low rates of efficacy and also have serious side effects. Exercise and relaxation techniques are generally safe, but of limited effectiveness (especially for those severely afflicted).

There is a need in the art for highly effective ways to treat sleep and stress disorders without risk of serious side effects.

SUMMARY

The present disclosure describes a headgear device that addresses the problems described above by delivering warm water vapor to the wearer's head, resulting in longer and higher quality sleep (although it is to be understood that not all embodiments of the device will address every problem described above).

Body temperature fluctuates during the circadian cycle. It is believed that the body needs a decreased body temperature for stress relief and sleep. When a person's temperature increases, sleep is difficult—when it decreases, one feels sleepy. Current models of sleep incorporate a "temperature sleep gate" for insomniacs: lower someone's core temperature quickly, and it induces sleep. Without wishing to be bound by any hypothetical model, it is believed that the devices and methods described herein accelerate the rate of lowering the body's internal thermostat to the required level for sleep, allowing insomniacs to quickly fall asleep and stay asleep up to and even beyond the required minimum six hours per night for good health.

In a first aspect, a therapeutic headgear device for the treatment of stress-related and sleep-related conditions is provided; the device comprises means for delivering heated water vapor to the crown of a wearer's head when worn; and means for retaining said heated water vapor in the vicinity of the wearer's head when worn.

In a second aspect, a headgear device is provided, comprising: a source of heated water vapor configured to deliver heated water to the crown of a wearer's head when the headgear device is worn; and a cap at least partially impermeable to water vapor, the cap configured to retain said heated water vapor in an area proximate to the crown when the headgear device is worn.

In a third aspect, a headgear device is provided, comprising: a cap body configured to be worn over the crown of a human wearer; and a heat source configured to heat water stored in an absorbent layer in the cap body. The cap body includes an outer layer that is at least partially water impermeable, and an absorbent layer configured to store water and disposed between the outer layer and the crown of the human wearer when the headgear device is worn.

In a fourth aspect, a method of treating or preventing a stress-related or sleep-related condition is provided. The method comprises: delivering heated water vapor to the crown of a wearer's head during sleep of the wearer to maintain a temperature at the skin ranging from normal human body temperature to about 110° F. The method may optionally employ the headgear of the first through third aspects.

The above presents a simplified summary in order to provide a basic understanding of some aspects of the claimed subject matter. This summary is not an extensive overview. It is not intended to identify key or critical elements or to delineate the scope of the claimed subject matter. Its sole purpose is to present some concepts in a simplified form as a prelude to the more detailed description that is presented later.

BRIEF DESCRIPTION OF THE DRAWINGS

FIG. 1 shows an embodiment of the headgear device and a wearer.

FIG. 2 shows an impermeable layer with built-in heating panels that is one of the layers in the embodiment of the headgear device shown in FIG. 1.

FIG. 3 shows an absorbent layer that fits inside the impermeable layer shown in FIG. 2 for use in the headgear device, partially constructed of terry cloth material which is attached to the inside of the cap.

FIG. 4 shows a layer in the embodiment of the headgear device shown in FIGS. 1-3, constructed of a plastic mesh material of fine porosity and permeable to vapor.

FIG. 5 shows a slim rechargeable and adjustable (polymer) battery-operated pack that may be set on the frontal part of the head cap as shown in FIG. 1. This embodiment of the battery pack is for powering the heating panels, and power lasts for several hours before recharging is necessary. The battery pack could also be set aside as an independent unit away from the head cap if the weight of the (polymer)

battery necessary to generate seven to eight hours of heat would be too heavy to be attached to the head cap.

FIG. 6 shows a cross section of an embodiment of the headgear device showing the three layers of the head cap: the plastic housing containing the heating source, terry cloth material for wetting, and plastic/mesh material.

FIG. 7 shows a rear view of an alternative embodiment of the device in the form of a backpack.

FIG. 8 shows a front view of an alternative embodiment of the device in the form of backpack device.

FIG. 9 shows an embodiment of the backpack device, including a rechargeable battery and adjustable straps to secure the backpack device to the wearer.

FIG. 10 shows an absorbent layer that is inserted into the out layer of the backpack device shown in FIG. 9.

FIG. 11 shows a diagram of an outer layer of the embodiment of the backpack shown in FIG. 9, showing the plastic housing containing a heating source comprising electrodes connected to a (polymer) battery.

FIG. 12 shows a vapor-permeable mesh layer that can be placed between the body of the wearer and the absorbent layer shown in FIG. 10.

DETAILED DESCRIPTION

A. Definitions

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terms "about" and "approximately" shall generally mean an acceptable degree of error or variation for the quantity measured given the nature or precision of the measurements. Typical, exemplary degrees of error or variation are within 20 percent (%), preferably within 10%, more preferably within 5%, and still more preferably within 1% of a given value or range of values. Numerical quantities given in this description are approximate unless stated otherwise, meaning that the term "about" or "approximately" can be inferred unless stated otherwise. Numerical quantities in the claims are exactly unless stated otherwise.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments.

The terminology used herein is for the purpose of describing particular embodiments only and is not intended to be limiting. As used herein, the singular forms "a", "an" and "the" are intended to include the plural forms as well, unless the context clearly indicates otherwise.

Spatially relative terms, such as "under", "below", "lower", "over", "upper" and the like, may be used herein for ease of description to describe one element or feature's relationship to another when the apparatus is right side up (i.e., worn by a standing subject).

The terms "first", "second", and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

Terms such as "at least one of A and B" should be understood to mean "only A, only B, or both A and B." The same construction should be applied to longer list (e.g., "at least one of A, B, and C").

The term "consisting essentially of" means that, in addition to the recited elements, what is claimed may also contain other elements (steps, structures, ingredients, components, etc.) that do not adversely affect the operability of what is claimed for its intended purpose as stated in this disclosure. This term excludes such other elements that adversely affect the operability of what is claimed for its intended purpose as stated in this disclosure, even if such other elements might enhance the operability of what is claimed for some other purpose.

The terms "treatment", "treat", and "treating" as used herein refers a course of action (such as the use of any embodiments of the headgear described herein) initiated after the onset of a clinical manifestation of a disease state or condition so as to eliminate or reduce such clinical manifestation of the disease state or condition. Such-treating need not be absolute to be useful.

The term "in need of treatment" as used herein refers to a judgment made by a caregiver that a patient requires or will benefit from treatment. This judgment is made based on a variety of factors that are in the realm of a caregiver's expertise, but that includes the knowledge that the patient is ill, or will be ill, as the result of a condition that is treatable by a method, compound or pharmaceutical composition of the disclosure.

The terms "prevention", "prevent", "preventing", "suppression", "suppress" and "suppressing" as used herein refer to a course of action (such as administering a compound or pharmaceutical composition of the present disclosure) initiated prior to the onset of a clinical manifestation of a disease state or condition so as to prevent or reduce such clinical manifestation of the disease state or condition. Such preventing and suppressing need not be absolute to be useful.

The term "in need of prevention" as used herein refers to a judgment made by a caregiver that a patient requires or will benefit from prevention. This judgment is made based on a variety of factors that are in the realm of a caregiver's expertise, but that includes the knowledge that the patient will be ill or may become ill, as the result of a condition that is preventable by a method, compound or pharmaceutical composition of the disclosure.

The term "individual", "subject" or "patient" as used herein refers to any animal, including mammals, such as mice, rats, other rodents, rabbits, dogs, cats, swine, cattle, sheep, horses, or primates, and humans. The term may specify male or female or both, or exclude male or female.

B. Headgear Device

A headgear device 100 is provided that delivers warm water vapor to the crown of a patient's head, which results in improved sleep and a reduction in stress. A general embodiment of the headgear device 100 comprises a means for delivering heated water vapor to the crown of a wearer's head when worn; and a means for retaining said heated water vapor in the vicinity of the wearer's head when worn. In this context the "crown" of the head is the surface on the top of the head, which is typically covered by hair in younger subjects (reference to "contact with the crown" can refer to contact with the hair, and does not necessarily refer to direct skin contact in every case). The device 100 may cover more of the subject's head in addition to the crown, including such parts as the ears, the forehead (in whole or in part), and the top of the neck. Some embodiments of the headgear 100 only partially cover the crown, while others cover the entire crown. Some embodiments cover the crown or a portion thereof, and do not cover other structures of the head; for example, various embodiments of the headgear 100 do not cover one or more of the ears, the forehead (in whole or in part), and the top of the neck.

Without wishing to be bound by any hypothetical model, it is believed that the headgear device 100 improves sleep by reducing body temperature. It is hypothesized that this occurs by absorbing latent heat near the wearer's head by vaporizing water near the head. This is unlike delivering sensible heat directly to body parts, which has the effect of raising body temperature.

One general embodiment of the headgear device 100 includes a source 120 of heated water vapor configured to deliver heated water to the crown of a wearer when the headgear device 100 is worn; and a cap 110 at least partially impermeable to water vapor, which retains the water vapor in an area proximate to the crown when the headgear device is worn. An alternative general embodiment of the device 100 comprises a cap body 110 configured to be worn over the crown of a human wearer, the cap body 110 including an outer at least partially water impermeable layer, and an absorbent layer configured to store water and disposed between the outer at least partially water impermeable layer and the crown of the human wearer when the headgear device 100 is worn; and a heat source 113 configured to heat water stored in the absorbent layer 120.

The device includes a source or means to deliver heated water vapor to the wearer's crown. This may be in any of numerous forms. The water vapor may be generated by devices such as a heated humidifier, an ultrasonic humidifier, a water vapor generator, or a steam generator. If generated by such a device the vapor may optionally be heated after generation or heated upon generation. The water vapor may then be routed to the user's crown by a hose or other conduit.

In the illustrated embodiments of the device 100 the water vapor is generated in the headgear device 100 near the patient's crown by heating an absorbent layer 120 containing some amount of liquid water. In the illustrated embodiment this takes the form of a terry cloth layer 120 (FIG. 3) that is wetted over a polymer mesh layer 130 (FIG. 4) that is in contact (or near contact) with the wearer's head and permeable to water vapor. In this embodiment the wet terry cloth 120 is heated to generate vapor that passes through the polymer mesh layer 130 and contacts the wearer's crown. The illustrated embodiment includes hook and loop fasteners 121 to fasten the absorbent layer 120 in the cap housing 110. Optionally the polymer mesh layer 130 could be included with a solid layer comprising a plurality of apertures.

In a simplified embodiment, water vapor is provided by a wet porous material (such as a textile or spongy material) in contact with the wearer's crown that is warmed by a heat source over the porous material.

Once generated, the warm water vapor is preferably retained near the crown. This can be accomplished in various ways. In the illustrated embodiment an impermeable plastic cap 110 is shown (FIG. 2) above (external to) the terry cloth layer 120 and the vapor-permeable plastic layer 130. Alternatively, other materials could be used that are at least partially impermeable to water vapor. The impermeable layer 110 may be constructed from waterproof fabric, such as those natural or synthetic fabrics that are laminated with a waterproofing material such as rubber, polyvinyl chloride (PVC), polyurethane (PU), silicone elastomer, fluoropolymers, wax, and a combination of any two or more of the foregoing. In a specific embodiment the impermeable layer 110 is made from nylon with a vinyl lining. In another specific embodiment the impermeable layer 110 is vinyl. Further suitable materials include: polypropylene-based foam, polyethylene-based foam, polyester foamed plastic sheet, polystyrene-based foam, plastic film, paper-foil laminate, foil, paper, non-woven, sponge, glass wool, fiberglass, and combinations thereof. The impermeable layer 110 will at least partially surround the crown in order to reduce losses of the vapor from the same area. In some embodiments of the device the impermeable layer 110 completely surrounds the crown, and contacts the head to form a mostly vapor-tight seal. In such embodiments the impermeable layer 110 may take the form of cap made of elastic material or having an elastic periphery. The cap may be fitted around the wearer's head by various means, such as by fasteners and straps; for example, the cap illustrated in FIG. 1 is secured by Velcro on an adjustable strap 111.

Some embodiments of the device comprise a heat source positioned to heat liquid water that is present in the device, such as in an absorbent or wettable layer. In the illustrated embodiment this takes the form of a hatch of heating panels 112. As shown, the heating panels 112 are connected by a network of the flexible electrodes 113 connected to a (polymer) battery operated power source 200 (detail in FIG. 5); and both the heating panels 112 and the flexible electrodes 113 are embedded in the compressible heating pad 110 as shown in FIG. 2. As the temperature in the heating pad rises, the liquid in the wetting material produces vapor. In a specific embodiment the heat source is configured to maintain a temperature of less than about 109.4° F. Alternatively another form of electric heating pad could be used, set to maintain a suitable temperature (e.g., less than about 109.4° F.).

The heat source may be configured to maintain a certain temperature or a certain range of temperatures. Some embodiments of the heat source are configured to maintain a temperature from about 99 to about 110° F. Further embodiments of the heat source may be configured to maintain temperatures within a range of 99.4-109.4° F. Specific embodiments of the heat source may be configured to maintain a temperature of any one of 99, 100, 101, 102, 103, 104, 105, 106, 107, 108, 109, 110° F., about any of the foregoing, and a range between any of the foregoing.

Temperatures in this paragraph refer to those at the surface of the heat source, such as the surface of a heating pad.

The heat source may be configured to cease heating after a certain period of time. Such period of time may roughly correspond to how long the wearer plans to sleep. Some embodiments of the heat source are configured to cease heating after a period of time has elapsed sufficient for the wearer to fall soundly asleep. For example, the heat source may be configured to cease heating after a period of time corresponding to the length of a typical sleep cycles, such as about 90-120 minutes. Some embodiments of the heat source may be configured to cease heating after about 2 hours. Further embodiments of the heat source may be configured to cease heating after about 1, 2, 3, 4, 6, or 8 hours. Further embodiments of the heat source may be configured to cease heating after 2-6 hours.

Turning to the embodiment of the device illustrated in the accompanying drawings, when powered up by the rechargeable (polymer) battery 200, water in the wetting material 120 is turned into vapor at a preselected temperature range of less than 109.4° F. The embodiment of the battery device 200 shown in FIG. 5 has a housing 201, AC plug 212, USB plug 211, USB socket 210, and activation setting marks 202. The streaming vapor escapes through the mesh lining material 130 (hypothesized to absorb latent heat of vaporization from the surrounding environment, principally the user's head and the resulting rapid cooling of the head/body temperature), inducing sleep and improving pain relief, blood vessel dilation and increased flow, relaxation, and reduced cardiac workload, hence, hypertension. When the heating cells 112 in the heating pad 110 are powered up, the (liquid) water in the wetting material 120 is turned into vapor and draws an amount of heat from its surrounding environment (in this case the user's head) usually equal to the temperature necessary to generate the vaporization.

Alternative embodiments of the device may be configured to deliver warm water vapor to other parts of the body, such as the joints (e.g., knees and shoulders) and back. One alternative embodiment, shown in FIGS. 7-12 is in the form of a backpack 300 comprising the same basic components as in the headgear device 100. A first embodiment of the backpack device 300 comprises a source of heated water vapor 310 configured to deliver heated water to the back of a wearer when the backpack device 300 is worn; and a covering 320 at least partially impermeable to water vapor, and configured to retain said heated water vapor in an area proximate to the back when the backpack device 300 is worn. A second embodiment of the backpack device 300 comprises means 310 for delivering heated water vapor to the wearer's back when worn; and means 320 for retaining said heated water vapor in the vicinity of the wearer's back when worn. A third embodiment of the backpack device 300 comprises a backpack body configured to be worn on the back of a human wearer, the backpack body including an outer at least partially water impermeable layer 320, and an absorbent layer 310 configured to store water and disposed between the outer at least partially water impermeable layer 320 and the back of the human wearer when the backpack device 300 is worn; and a heat source configured to heat water stored in the absorbent layer 310. Various straps 301 and fasteners 303, 304 (such as hook-and-loop fasteners) can be used to secure the backpack device 300 to the wearer. A vapor-permeable mesh layer 330 may be used between the absorbent layer 310 and the wearer. Some embodiments of the backpack device include a heating device built into the impermeable layer 320, such as shown in FIG. 11. The embodiment of the impermeable layer 320 in FIG. 11 includes heating panels 112 and flexible electrodes 113 to heat the underlying absorbent layer 310 to create warm water vapor.

Without wishing to be limited to any given hypothetical model, the mechanism of action is believed to depend on the latent heat of vaporization, which is believed to be inversely correlated with the lowering of body temperature and the dilation of blood vessels. As it applies particularly to this invention, when the heating cells in the heating pad are powered up, the liquid (water) in the wetting material begins to vaporize, which is believed to draw latent heat from the user's head/body and head in particular and rapidly cooling the user's core body temperature to induce sleep while relieving stress-related pains such as stiff muscles and joints, nerve pain, and back pain. The resulting escaping heat from the user's head/body which is believed to take the form of body sweat which over a preselected period of use of four to six hours can be substantial.

C. Method of Treating and Preventing Sleep and Anxiety Related Disorders

A method of treating and/or preventing a stress-related or sleep-related condition, the method comprising: delivering heated water vapor to the crown of a wearer's head during sleep of the wearer to maintain a temperature at the crown exceeding normal human body temperature (as would be measured by placing a thermometer between the crown and the headgear device). As explained above (and without wishing to be bound by any particular hypothetical model), it is believed that this results in an accelerated reduction in body temperature (at least locally) facilitated by the absorption of latent heat from the wearer's body. Normal human body temperature can range from 97-99° F. for adults, which can serve as the minimum temperature that is maintained at the crown. The temperature maintained at the crown will in some embodiments not exceed about 110° F. The maintained temperature may be in some embodiments 97, 98, 99, 100, 101, 102, 103, 104, 105, 106, 107, 108, 109, 110° F., about any of the foregoing, and a range between any two of the foregoing. In a specific embodiment of the method the crown is maintained at a temperature of 100-110° F., or more specifically 100.7-109.4° F.

The stress or sleep-related disorder may be any that is a symptom of or a cause of stress or sleep problems. Such symptoms and causes include: trouble focusing the attention, lack of attention to sensory input, increased human error resulting in accidents, longer reactions times, excessive yawning, moodiness, fatigue, irritability, depression, learning difficulties, forgetfulness, anxiety, lack of motivation, clumsiness, increased appetite, reduced libido, weakened immune system, increased insulin release, cardiovascular disease, hypertension, stroke, diabetes, psychosis, hallucination, post-traumatic stress disorder (PTSD), acute stress disorder (ASD), depression, anxiety, obsessive-compulsive disorder (OCD), an eating disorder, anorexia nervosa, lack of energy, headache, upset stomach, diarrhea, constipation, nausea, muscle aches, back pain, joint pain, chest pain, tachycardia, insomnia, increased infections, sexual dysfunction, tinnitus, excessive perspiration, xerostomia, dysphagia, and bruxism. The subject may be in need of treatment, prevention, or both, as concerns any one or more of the foregoing.

Some embodiments of the method comprise ceasing the delivery of the water vapor to the crown when the subject wakes. Further such embodiments of the method may comprise abstaining from delivering the water vapor to the crown during waking hours prior to the subject retiring for sleep. The method is believed to be most effective when used during sleep to encourage and enhance sleep; thus in some cases the treatment will not be administered until the subject retires for sleep.

The crown temperature will be maintained sufficiently long to allow the wearer to fall asleep, in some cases long enough to ensure an adequate period of deep sleep. Such period of time may roughly correspond to how long the wearer plans to sleep. In some embodiments of the method the crown temperature is maintained for a period of time sufficient for the wearer to fall soundly asleep. For example, the crown temperature may be maintained for a period of time corresponding to the length of a typical sleep cycle, such as about 90-120 minutes. In some embodiments of the method the crown temperature is maintained for at least 2 hours. In some embodiments of the method the crown temperature is maintained for 1, 2, 3, 4, 6, or 8 hours, about any of the foregoing, or up to any of the foregoing. In some embodiments of the method the crown temperature is maintained for up to 2-6 hours.

The method may comprise evaporating liquid water to form the heated water vapor. The liquid may be evaporated from the proximity of the crown, as would occur using the illustrated embodiments of the headgear device. In such embodiments liquid water is evaporated from an absorbent layer of material in contact with the crown or in close proximity to the crown. In specific embodiments of the method the absorbent layer is in contact with the crown, or separated from the crown by a vapor-permeable layer. The absorbent layer and vapor-permeable layer may be any disclosed as suitable for use in the headgear device 100. Evaporation may be achieve by various methods, including by heating the liquid water. The liquid water may be heated while present in the absorbent layer. Heat may be delivered by an electric heating device (such as any disclosed above as suitable in the headgear device 100) in close contact with the liquid water, or by transporting a heated fluid (such as steam or hot water) into contact with the liquid water. In the illustrated embodiment the water is heated by an electric heating pad comprising a plurality of heating panels 112 and flexible electrodes 113.

The method may achieve reduced body temperatures as measured with an oral digital thermometer. In some embodiments of the method body temperature is reduced below 98.6° F. In further embodiments of the method body temperature is reduced below 98° F. In further embodiments of the method body temperature is reduced to 94-98° F. All of the foregoing temperatures refer to such temperatures as measured by a digital oral thermometer. Without wishing to be bound by any hypothetical model, it is believed that the method facilitates rapid and lasting sleep by accelerating the normal drop in core body temperature that occurs during sleep.

The method may be repeated during multiple periods of sleep. Regular use of the method, or periodic repetition of the method, may enhance the resultant reduction in symptoms of stress and sleep related disorders. Some embodiments of the method comprise repeating the application of heated water vapor during two or more consecutive sleep periods. Further such embodiments may involve repetition during 2, 3, 4, 5, 6, 7, 14, 21, and 28 consecutive sleep periods. Further such embodiments may involve nightly use of the method for certain periods; exemplary such periods are one week, one month, three months, six months, and a year.

D. Example 1: Treatment of Insomnia and Hypertension

Subject 1 was a chronic insomniac. Subject 1 has used an embodiment of the headgear device consistently for over 20 years. An improvised embodiment of the headgear device was used, comprising a damp terry cloth bath cloth in contact with the crown, a small electric heating pad on the bath cloth, and a shower cap over the other layers. A timer was used to maintain elevated temperature of the heating pad for six hours. Subject 1 reported falling asleep within 3-5 minutes of activation of the heating pad, and remaining asleep for approximately 8½ hours. Subject 1 reported complete disappearance of insomnia when the device was used in this manner.

Subject 1 self-measured the temperature of the device and his own body temperature on several occasions. The results are shown in Table 1. Usually a first measurement was taken immediately before bed at about 9:30 PM, followed by one or more measurements taken during the night. Temperature of the device was measured between the heating pad and the bath cloth (C&T), and between the bath cloth and the subject's head (T&H). The subject self-measured body temperature using a RELION digital oral thermometer. The subject self-measured blood pressure occasionally.

TABLE 1

TEMPERATURE AND BLOOD PRESSURE MEASUREMENTS

| Date | Time | T (C & T) ° F. | T (T & H) ° F. | Body T ° F. | BP S/D mmHg | BP S/D mmHg The Day After |
|---|---|---|---|---|---|---|
| Nov. 2, 2012 | 9:42 pm | 99.4° F. | 98.8° F. | 97.6° F. | 134/87 | |
| Nov. 2, 2012 | 10:02 pm | 100.7° F. | 103.6° F. | 96.8° F. | | |
| Nov. 2, 2012 | 11:12 pm | 107.9° F. | 107.0° F. | 93.6° F. | | |
| Dec. 3, 2012 | 2:38 am | 108.3° F. | 106.1° F. | 93.1° F. | | 127/84 |
| Nov. 15, 2012 | 9:38 pm | 102.4° F. | 101.1° F. | 98.8° F. | 128/80 | |
| Nov. 15, 2012 | 10.00 pm | 104.2° F. | 103.9° F. | 97.6° F. | | |
| Nov. 16, 2012 | 1:00 am | 106.1° F. | 105.7° F. | 95.9° F. | | 123/74 |
| Nov. 27, 2012 | 9:30 pm | 103.2° F. | 103.0° F. | 97.6° F. | 124/76 | |
| Nov. 27, 2012 | 10:15 pm | 107.7° F. | 105.5° F. | 94.2° F. | | |
| Nov. 28, 2012 | 4:55 am | 109.4° F. | 108.3° F. | 97.4° F. | | 117/69 |

Reduction in body temperature was observed during all six recorded durations of usage. The lowest body temperature recorded during all six test periods was 93.1° F. on Nov. 3, 2012 at 3:38 am, after about six hours of wearing the device and waking up by alarm clock at 11:12 pm the previous evening to re-wet the wetting cloth. Corresponding temperatures were 108.3° F. between the head cap and the wetting material, and 106.1° F. between the wetting material and the scalp. Also as expected, the recorded body temperatures were consistently lower than the recorded temperatures between the head cap and the wetting material and between the wetting material and the scalp, respectively, believed to be an indication of the latent heat of vaporization effect. Columns six and seven report the blood pressure S/D (mm Hg) findings. Column six reports the blood pressure S/D mmHg findings at 7 AM on the morning before the overnight use of the headgear device; and column seven reports blood pressure S/D (mm Hg) at 7 AM the following morning, exactly twenty-four hours after the previous measurement in order to isolate all other probable intervening variables. Blood pressure went down from 134/87 to 123/74 S/D mm Hg which was consistent with the observations on November 27th and 28th of a drop from 124/76 to 117/69 S/D mm Hg.

E. Example 2: Treatment of Anorexia Nervosa

Subject 2, an undergraduate student, tested the same prototype of the device described in Example 1. Subject 2 reported falling asleep for the first time in about four days while heavily sedated in a health clinic while undergoing treatment for anorexia nervosa. She was able to return to campus a few days later. She reported that her symptoms of anorexia nervosa were improved. Applicant judged her appearance to be significantly improved as well.

F. Example 3: Post-Traumatic Stress Disorder

Subject 3 was an excellent student who suddenly began missing classes frequently. Subject 3 confided his sleeplessness and severe mental fatigue due to his PTSD and agreed to test the headgear device. The subject had at times suffered such severe insomnia that the subject went for several days with little or no sleep. Subject 3 proceeded to use a prototype similar to the one described in Example 1. Subject 3 reported that the device induced rapid relaxation that allowed for several hours of relaxed and uninterrupted sleep. Subject 3 compared the device favorably to prescription sleep medications he had previously tried.

G. Example 4: Functional Stomach Stress Disorder

Subject 4 was a boy aged 14 who, although normally a good student, had missed school five times within a month. Following a diagnosis of "functional stomach stress disorder" related to his being severely stressed (diarrhea, vomiting, sleeplessness and crying) due to health issues in his immediate family, Subject 4 was prescribed Fluoxetine HCL, 10 mg CAPs. The medication carried the possibility of side effects such as hallucinations, so as an alternative the headgear device was used. The subject was able to resume school the next day, and continues to use the headgear device every time his stress symptoms threaten to resume.

H. Conclusions

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

I claim:

1. A method of treating or preventing a stress-related or sleep-related condition, the method comprising: delivering heated water vapor to the crown of a wearer's head while the wearer sleeps to maintain a temperature at the crown exceeding normal human body temperature, wherein the heated water vapor is delivered by a cap worn on the head of the wearer.

2. The method of claim 1, wherein the temperature at the crown is maintained at about 98-110° F.

3. The method of claim 1, wherein the temperature at the crown is maintained for at least 90 minutes.

4. The method of claim 1, wherein the temperature at the crown is maintained for no more than 8 hours.

5. The method of claim 1, wherein the heated water vapor selectively contacts the crown of the wearer's head, and does not contact other portions of the wearer's body.

6. The method of claim 1, wherein the stress-related or sleep-related condition is selected from one or more of: trouble focusing attention, lack of attention to sensory input, increased human error resulting in accidents, longer reaction times, excessive yawning, moodiness, fatigue, irritability, depression, learning difficulties, forgetfulness, anxiety, lack of motivation, clumsiness, increased appetite, reduced libido, weakened immune system, increased insulin release, cardiovascular disease, hypertension, stroke, diabetes, psychosis, hallucination, post-traumatic stress disorder (PTSD), acute stress disorder (ASD), depression, anxiety, obsessive-compulsive disorder (OCD), an eating disorder, anorexia nervosa, lack of energy, headache, upset stomach, diarrhea, constipation, nausea, muscle aches, back pain, joint pain, chest pain, tachycardia, insomnia, increased infections, sexual dysfunction, tinnitus, excessive perspiration, xerostomia, dysphagia, and bruxism.

7. The method of claim 1, wherein the stress-related or sleep-related condition is selected from one or more of: posttraumatic stress disorder, pain, back pain, joint pain, anxiety, insomnia, elevated cardiac workload, functional stomach stress disorder, anorexia nervosa, and hypertension.

8. The method of claim 1, wherein the subject is in need of treatment or prevention of the stress-related or sleep-related condition.

9. The method of claim 1, further comprising passing the heated water vapor through a mesh contacting the crown.

10. The method of claim 1, wherein the cap comprises an outer layer constructed of an elastic material.

11. The method of claim 1, wherein the cap comprises an outer layer that is at least partially moisture-impermeable.

12. The method of claim 1, wherein the cap comprises an absorbent layer in contact with the crown of the head; and a heating pad positioned to raise the temperature of the absorbent layer sufficiently to generate the water vapor when water is present in the absorbent layer.

13. The method of claim 1, further comprising ceasing the delivery of heated water vapor after a predetermined duration of time.

14. The method of claim 1, wherein the heated water vapor is delivered to the crown of the wearer's head during multiple sleep periods on consecutive days.

15. The method of claim 1, wherein the cap is part of a headgear device, the headgear device comprising:
   (a) a source of heated water vapor configured to deliver heated water to the crown of the wearer when the headgear device is worn; and
   (b) the cap, wherein the is at least partially impermeable to water vapor and the cap is configured to retain said heated water vapor in an area proximate to the crown when the headgear device is worn.

16. A method of treating or preventing a stress-related or sleep-related condition, the method comprising: delivering heated water vapor to the crown of a wearer's head while the wearer sleeps to maintain a temperature at the crown exceeding normal human body temperature, wherein the heated water vapor is delivered by a therapeutic headgear device comprising:
   (a) means for delivering heated water vapor to the crown of the wearer's head when worn; and
   (b) means for retaining said heated water vapor in a vicinity of the wearer's head when worn.

* * * * *